(12) United States Patent
Shin et al.

(10) Patent No.: US 11,123,114 B2
(45) Date of Patent: Sep. 21, 2021

(54) PERCUTANEOUS SCREW FIXING ROD INSERTING DEVICE FOR SCREW HEAD ALIGNMENT IN MINIMALLY INVASIVE SURGERY

(71) Applicants: Daewon Shin, Yorba Linda, CA (US); Anthony Hunkyun Sin, Shreveport, LA (US); Sean Keem, Mercer Island, WA (US); Seung Hwan Yoon, Seoul (KR)

(72) Inventors: Daewon Shin, Yorba Linda, CA (US); Anthony Hunkyun Sin, Shreveport, LA (US); Sean Keem, Mercer Island, WA (US); Seung Hwan Yoon, Seoul (KR)

( * ) Notice: Subject to any disclaimer, the term of this patent is extended or adjusted under 35 U.S.C. 154(b) by 0 days.

(21) Appl. No.: 17/069,694

(22) Filed: Oct. 13, 2020

(65) Prior Publication Data

US 2021/0161569 A1 Jun. 3, 2021

(30) Foreign Application Priority Data

Nov. 29, 2019 (KR) .......................... 10-2019-0156585

(51) Int. Cl.
*A61B 17/70* (2006.01)
(52) U.S. Cl.
CPC ...... *A61B 17/7089* (2013.01); *A61B 17/7001* (2013.01)
(58) Field of Classification Search
CPC .............. A61B 17/708; A61B 17/7085; A61B 17/7089; A61B 17/7077
See application file for complete search history.

(56) References Cited

U.S. PATENT DOCUMENTS

| | | | |
|---|---|---|---|
| 7,993,344 B2 | 8/2011 | Pond, Jr. et al. | |
| 8,075,592 B2 | 12/2011 | Landry et al. | |
| 8,333,770 B2 * | 12/2012 | Hua | A61B 17/7032 606/86 A |
| 9,055,934 B2 * | 6/2015 | DiPoto | A61B 17/8863 |

(Continued)

FOREIGN PATENT DOCUMENTS

| | | |
|---|---|---|
| KR | 10-2011-0029988 A | 3/2011 |
| KR | 10-1703003 B1 | 2/2017 |
| WO | WO-2020219018 A1 * 10/2020 ......... A61B 17/7085 |

*Primary Examiner* — Julianna N Harvey
(74) *Attorney, Agent, or Firm* — Novick, Kim & Lee, PLLC; Sang Ho Lee; Hyun Woo Shin

(57) ABSTRACT

Provided is a percutaneous screw fixing rod inserting device for minimal invasive surgery, which includes: a leg unit including a plurality of support legs, each of which has a joint link provided at a lower end thereof; an aligning holder unit configured to align the plurality of support legs such that longitudinal central axes of the support legs of the leg unit are placed on one virtual plane, the aligning holder unit holding the support legs such that an angle between the longitudinal central axes of the support legs is maintained; and a rod inserting unit coupled to the aligning holder unit to rotate by a predetermined angle around a portion coupled to the aligning holder unit and configured to insert the rod into a rod insert hole provided to the joint link of the support leg, thereby eliminating the difficulty of inserting the rod caused by the misalignment of the pedicle screws and increasing the convenience or efficiency of the medical procedure.

9 Claims, 18 Drawing Sheets

(56) References Cited

U.S. PATENT DOCUMENTS

| | | | |
|---|---|---|---|
| 2002/0161368 A1* | 10/2002 | Foley | A61B 17/8897 |
| | | | 128/898 |
| 2008/0300638 A1* | 12/2008 | Beardsley | A61B 17/7032 |
| | | | 606/306 |
| 2010/0114179 A1* | 5/2010 | Moore | A61B 17/7032 |
| | | | 606/308 |
| 2012/0109208 A1* | 5/2012 | Justis | A61B 17/7089 |
| | | | 606/264 |
| 2014/0277151 A1* | 9/2014 | Fowler | A61B 17/7074 |
| | | | 606/265 |
| 2015/0088210 A1* | 3/2015 | Reitblat | A61B 17/7083 |
| | | | 606/86 A |
| 2016/0206442 A1* | 7/2016 | Dvorak | A61F 2/4611 |
| 2016/0331410 A1* | 11/2016 | Tsuang | A61B 17/7037 |

* cited by examiner

PERCUTANEOUS SCREW FIXING ROD INSERTING DEVICE FOR SCREW HEAD ALIGNMENT IN MINIMALLY INVASIVE SURGERY

CROSS-REFERENCE TO RELATED APPLICATIONS

This application claims priority to Korean patent application No. 10-2019-0156585 filed in the Korean Intellectual Property Office on Nov. 29, 2019, the entire contents of which is hereby incorporated by reference.

TECHNICAL FIELD

This disclosure relates to a device for solving the problem that screw heads are not aligned in one plane due to the crossing of screw towers that occurs between the lumbar spine No. 5 and the front spine No. 1 during minimally invasive surgery, and for maintaining the alignment of the screw heads.

BACKGROUND ART

Various medical procedures have been proposed and used in medical fields to treat problems that occur in the spine disk due to aging or an accident.

Among these medical procedures, there is bone fusion in which pedicle screws are inserted and fixed into the spine at upper and lower parts of the damaged disk and then a rod is fastened to the pedicle screws to secure the gap between the spines so that the bone is fused normally. The conventional bone fusion is a surgical method conducted by cutting the skin at the center line of the spine, cutting the posterior muscle, and by removing all tissues and muscles to the site where the spine screw is inserted. This surgical method has disadvantages such as bleeding caused by many incisions, prolonged operation time, postoperative pain, scars, and long recovery time.

A minimally invasive surgery is a surgical method that is designed to overcome these shortcomings. The minimally invasive surgery is a surgical method that may give the same effects and results as the conventional surgery but with minimal incisions, and recently, most surgeries are performed in this way.

In addition, in the minimally invasive surgery, a rod inserting device is used to fasten a rod to a pedicle screw. Among the technologies related to the rod inserting device, there is U.S. Pat. No. 7,993,344 (title: guide and method for inserting an elongate member into a patient, hereinafter referred to as the prior literature).

As shown in FIG. 16 of the prior literature, in order to fix a pedicle screw 90, a plurality of screw holders 103 having a pipe-like shape are twisted and staggered differently from the alignment direction of screw heads. Since the plurality of screw holders are obliquely staggered, it is difficult to maintain the aligned state to fix the pedicle screw. Also, when a rod 30 is inserted, it is difficult to insert the rod due to misalignment, which makes the operation difficult.

As described above, it is difficult to maintain the aligned state to fix the pedicle screw, and it is also difficult to insert the rod due to unstable alignment. Further, the pedicle screw system fixed under the unstable alignment tends to result in spine instability after surgery, which may result in an operation failure where reoperation is inevitable.

DISCLOSURE

Technical Problem

The present disclosure is designed to solve the problems of the conventional art as described above, and the present disclosure is directed to providing a percutaneous screw fixing rod inserting device for minimally invasive surgery, which may allow a rod to be inserted in a state in which a plurality of support legs are aligned while maintaining a constant angle.

Technical Solution

In one embodiment, there is provided a percutaneous screw fixing rod inserting device for minimal invasive surgery, including: a leg unit including a plurality of support legs, each of the plurality of support legs having a joint link disposed at a lower end thereof, wherein the joint link includes a rod insert hole and is configured to mediate coupling between a rod and a screw head of a pedicle screw configured to fix to a spine; an aligning holder unit holding the plurality of support legs and configured to align the plurality of support legs, wherein longitudinal central axes of the plurality of support legs are on one virtual plane and an angle between the longitudinal central axes of the plurality of support legs is maintained; and a rod inserting unit coupled to the aligning holder unit and configured to rotate by a predetermined angle around a portion coupled to the aligning holder unit and to insert the rod into the rod insert hole of the joint link of the each of the plurality of support legs.

In another embodiment, the each of the plurality of support legs has a partial upper portion which is inclined and the partial upper portions of adjacent support legs come into contact with each other to set the angle between the longitudinal central axes thereof, and the aligning holder unit has a plurality of leg holding holes and the partial upper portion of the each of the plurality of support legs are respectively inserted into and held in corresponding each of the plurality of leg holding holes.

In another embodiment, the plurality of leg holding holes are formed at a lower side of the aligning holder unit and the partial upper portions of the plurality of support legs are respectively inserted therein, and at an inner side of the aligning holder unit, the plurality of leg holding holes are shaped corresponding to a shape of outer surfaces of the plurality of support legs whose partial upper portions are in contact with each other.

In another embodiment, the aligning holder unit has a center hole formed at an upper end thereof to communicate with the plurality of leg holding holes, the each of the plurality of support legs has an empty space formed therein, and the pedicle screw is configured to be inserted into the center hole, move to the joint link disposed at the lower end of the support leg, and to be fixed to the spine.

In another embodiment, the each of the plurality of support legs has an aligning guide hole formed by cutting at least a portion of an outer circumference of the support leg in a longitudinal direction, and the each of the plurality of leg holes has an aligning guide protrusion formed adjacent thereto, and at least a portion of the aligning guide protrusion is configured to be inserted into a corresponding aligning guide hole of the support leg and to guide the support leg to be inserted into the leg holding hole of the aligning holder unit in the longitudinal direction.

In another embodiment, the portion of the aligning guide protrusion is configured to be inserted into the corresponding aligning guide hole and the support leg rotates around a longitudinal central axis thereof.

In another embodiment, a segmentation groove is formed at an upper side of the joint link and the joint link disposed at the lower end of the support leg is configured to separate from the support leg.

In another embodiment, the rod inserting unit includes a rod holder configured to hold the rod at one side end thereof, wherein the rod is selectively mounted thereto or detached therefrom; and a swing body supporting the rod holder and having one side end thereof hinge coupled to an other side end of the rod holder, wherein the rod holder is configured to rotate by a certain angle.

In another embodiment, an other side end of the swing body is coupled to a portion of the aligning holder unit, and the swing body is configured to rotate by the certain angle around the coupled portion.

In yet another embodiment, the other side end of the swing body and the portion of the aligning holder unit is selectively and detachably coupled.

Advantageous Effects

In the percutaneous screw fixing rod inserting device for minimal invasive surgery according to the present disclosure, the rod may be inserted into the rod insert hole in a state where the alignment of the plurality of support legs is maintained. Therefore, the difficulty of inserting the rod due to the misalignment of the pedicle screws is eliminated, and furthermore, the convenience or efficiency of the medical procedure is increased.

BEST MODE

Hereinafter, a preferred embodiment will be described with reference to the accompanying drawings in order to understand the present disclosure in more detail.

Figure 8:
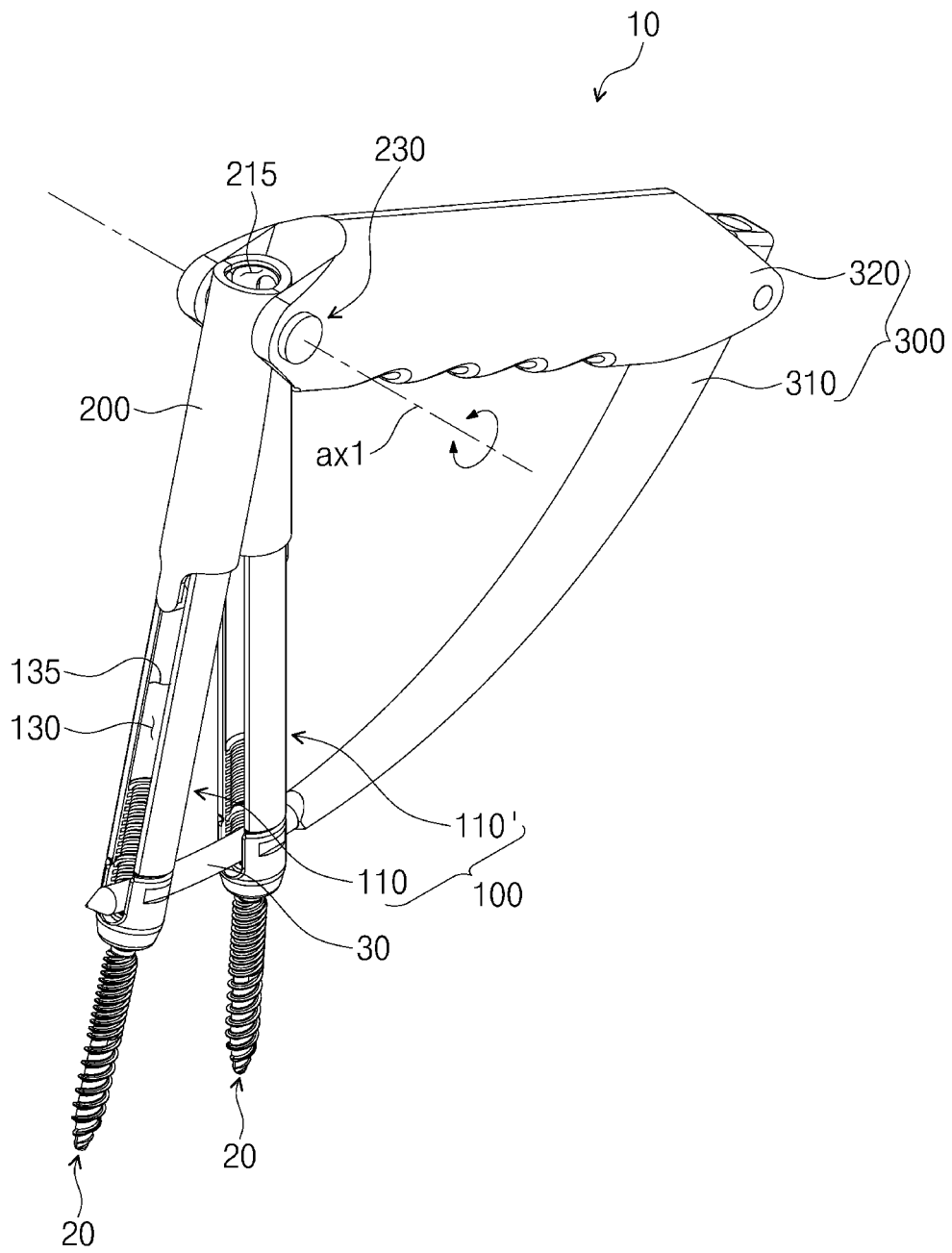
FIG. 8 is a perspective view schematically showing a percutaneous screw fixing rod inserting device for minimal invasive surgery according to an embodiment of the present disclosure.

FIG. 8 is a perspective view schematically showing a percutaneous screw fixing rod inserting device for minimal invasive surgery according to an embodiment of the present disclosure.

Referring to FIG. 8, a screw fixing rod inserting device 10 for minimal invasive surgery according to an embodiment of the present disclosure includes a leg unit 100, an aligning holder unit 200, and a rod inserting unit 300.

Here, the leg unit 100 will be described with reference to FIGS. 1 to 3.

Figure 1:
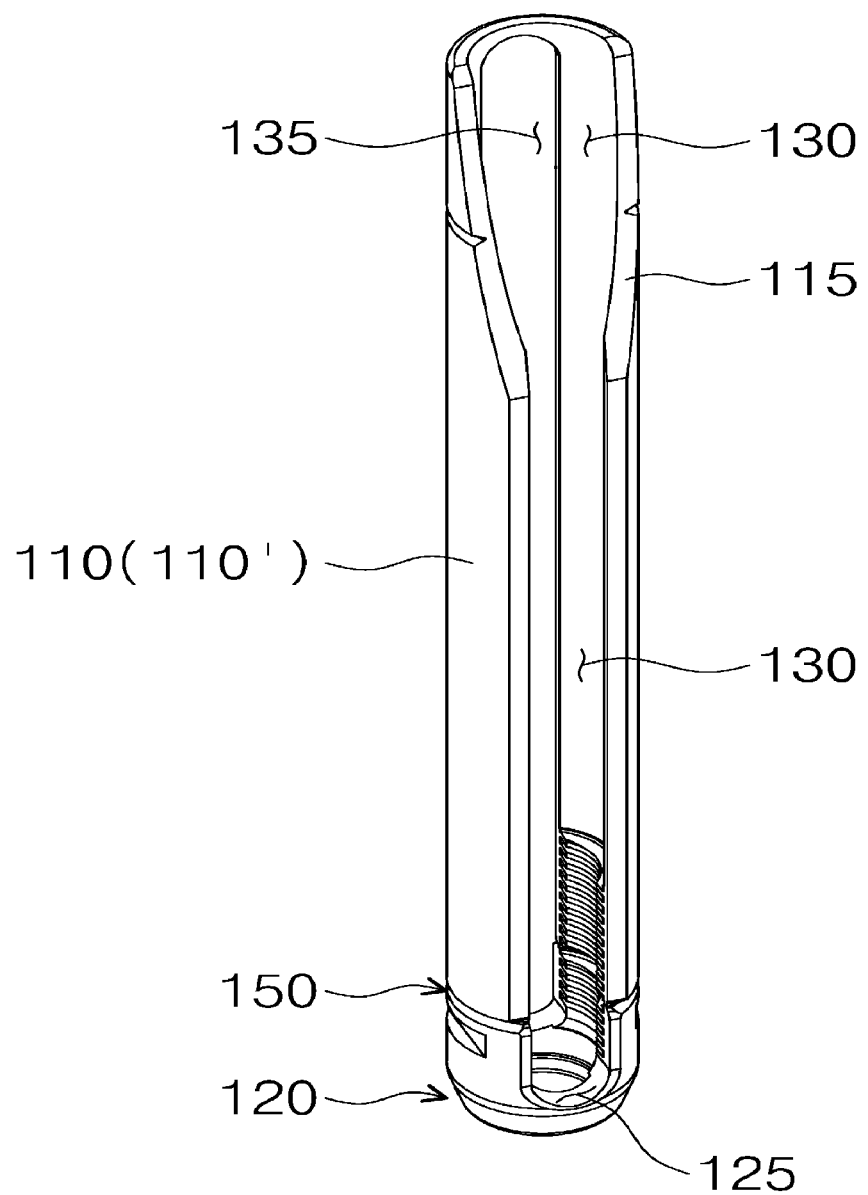
FIG. 1 is a perspective view schematically showing a support leg in a percutaneous screw fixing rod inserting device for minimal invasive surgery according to an embodiment of the present disclosure.
Figure 2:
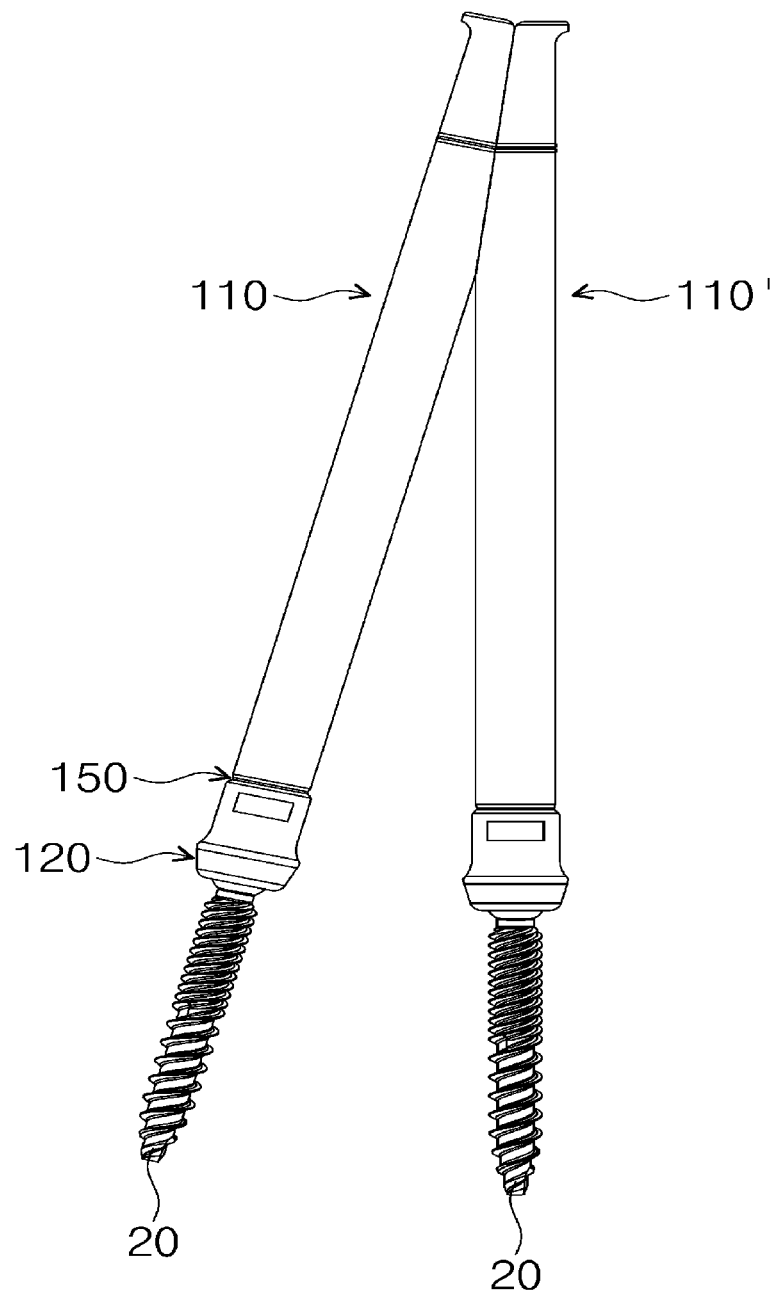
FIG. 2 is a side view schematically showing neighboring support legs in the percutaneous screw fixing rod inserting device for minimal invasive surgery according to an embodiment of the present disclosure.
Figure 3:
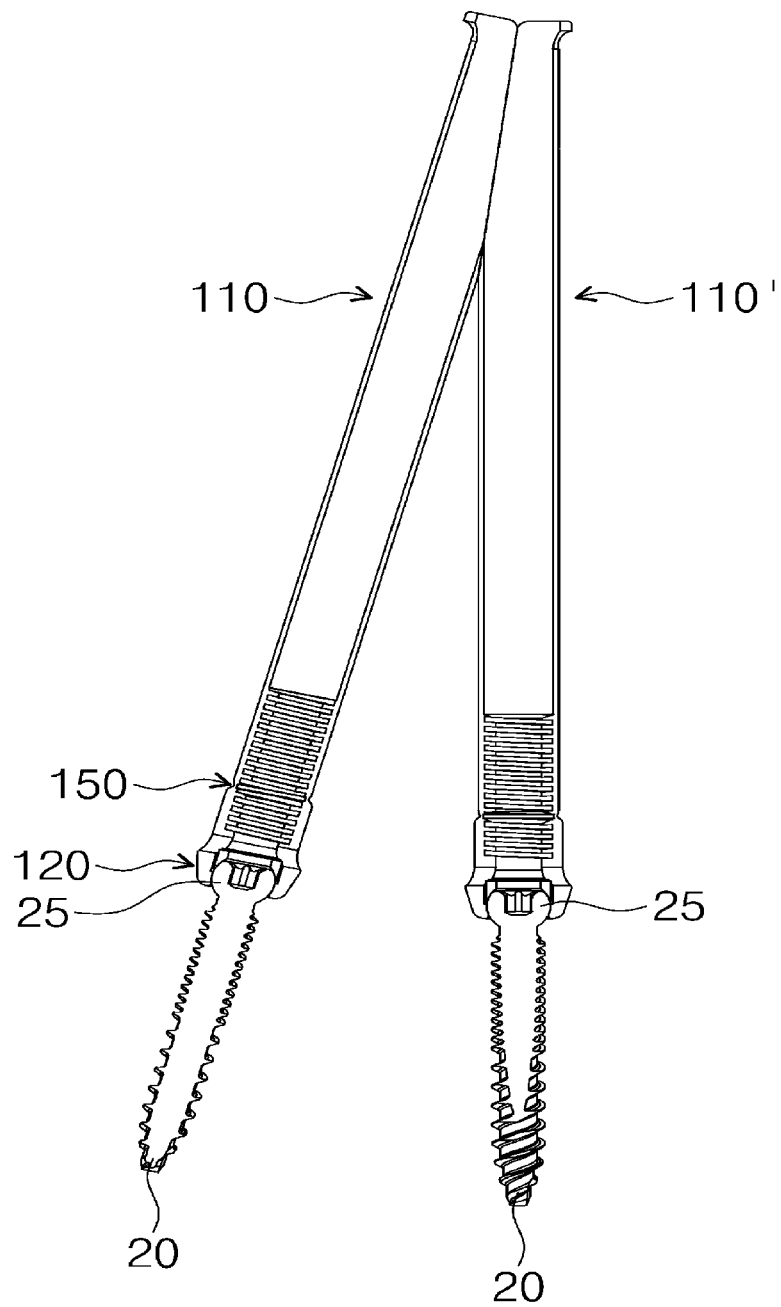
FIG. 3 is a side sectional view schematically showing the neighboring support legs in the percutaneous screw fixing rod inserting device for minimal invasive surgery according to an embodiment of the present disclosure.

FIG. 1 is a perspective view schematically showing a support leg in the percutaneous screw fixing rod inserting device for minimal invasive surgery according to an embodiment of the present disclosure, FIG. 2 is a side view schematically showing neighboring support legs in the percutaneous screw fixing rod inserting device for minimal invasive surgery according to an embodiment of the present disclosure, and FIG. 3 is a side sectional view schematically showing the neighboring support legs in the percutaneous screw fixing rod inserting device for minimal invasive surgery according to an embodiment of the present disclosure.

Referring to FIGS. 1 to 3, a leg unit 100 includes a plurality of support legs 110, 110' for supporting a pedicle screw 20 to be fixed to the spine. In an embodiment of the present disclosure, two support legs 110, 110' are provided as an example.

The support leg 110, 110' has a certain length as shown in the figures, and a joint link 120 for mediating the coupling between a screw head 25 of the pedicle screw 20 fixed to the spine and a rod 30 is provided at a lower end of the support leg 110, 110'.

The support leg 110, 110' has an empty space 130 formed therein to have a pipe-like shape. A thread is formed at a portion of an inner surface of the support leg 110, 110' so that the pedicle screw 20 is inserted therein and fixed to the spine.

In addition, partial upper portions 115 of neighboring support legs 110, 110' are formed to be inclined with respect to a longitudinal central axis so that an angle may be set to the longitudinal central axis while the partial upper portions 115 of the support legs 110, 110' are in contact with each other.

As shown in FIG. 2 or 3, as the partial upper portions 115 inclined at the support legs 110, 110' come into contact with each other, an angle may be set between the neighboring support legs 110, 110', and the angle between the neighboring support legs 110, 110' is maintained as being held by an aligning holder unit 200, explained later.

In addition, the support leg 110, 110' has an aligning guide hole 135 formed by cutting at least a portion of an outer circumference of the support leg 110, 110' in a longitudinal direction. A portion of an aligning guide protrusion 235 of the aligning holder unit 200, explained later, is inserted into the aligning guide hole 135 so that the support legs 110, 110' are maintained in an aligned state without shaking.

The joint link 120 provided at one end of the support leg 110, 110' has a rod insert hole 125 into which the rod 30 is inserted.

In this embodiment, the rod insert hole 125 is formed to be connected to the aligning guide hole 135 as shown in the figures. However, it is also possible that the rod insert hole 125 and the aligning guide hole 135 are not connected but are separated from each other.

The rod insert holes 125 are preferably formed in the joint links 120 of the neighboring support legs 110, 110' so that the central axis of the rod 30 may be disposed on the same virtual plane as the longitudinal central axes of the neighboring support legs 110, 110'.

If the rod insert hole 125 is formed in the joint link 120 as described above, the rod 30 may be easily inserted into the rod insert hole 125 while maintaining the alignment of the pedicle screw 20. Therefore, it is possible to eliminate the difficulty in inserting the rod 30 caused by the misalignment of the pedicle screw 20.

In addition, the joint link 120 has a segmentation groove 150 formed at an upper side thereof so as to be separable from the support legs 110, 110'.

After the rod 30 is inserted into the rod insert hole 125 of the joint link 120, a bolt (not shown) is bolted at an upper side of the joint link 120 to press and fix the rod 30. In this case, the support legs 110, 110' should be separated while leaving the joint link 120.

Therefore, the segmentation groove 150 is preferably provided so that the joint link 120 may be easily segmented and separated from the support legs 110, 110'.

Next, the aligning holder unit 200 will be described with reference to FIGS. 4 to 6.

Figure 4:
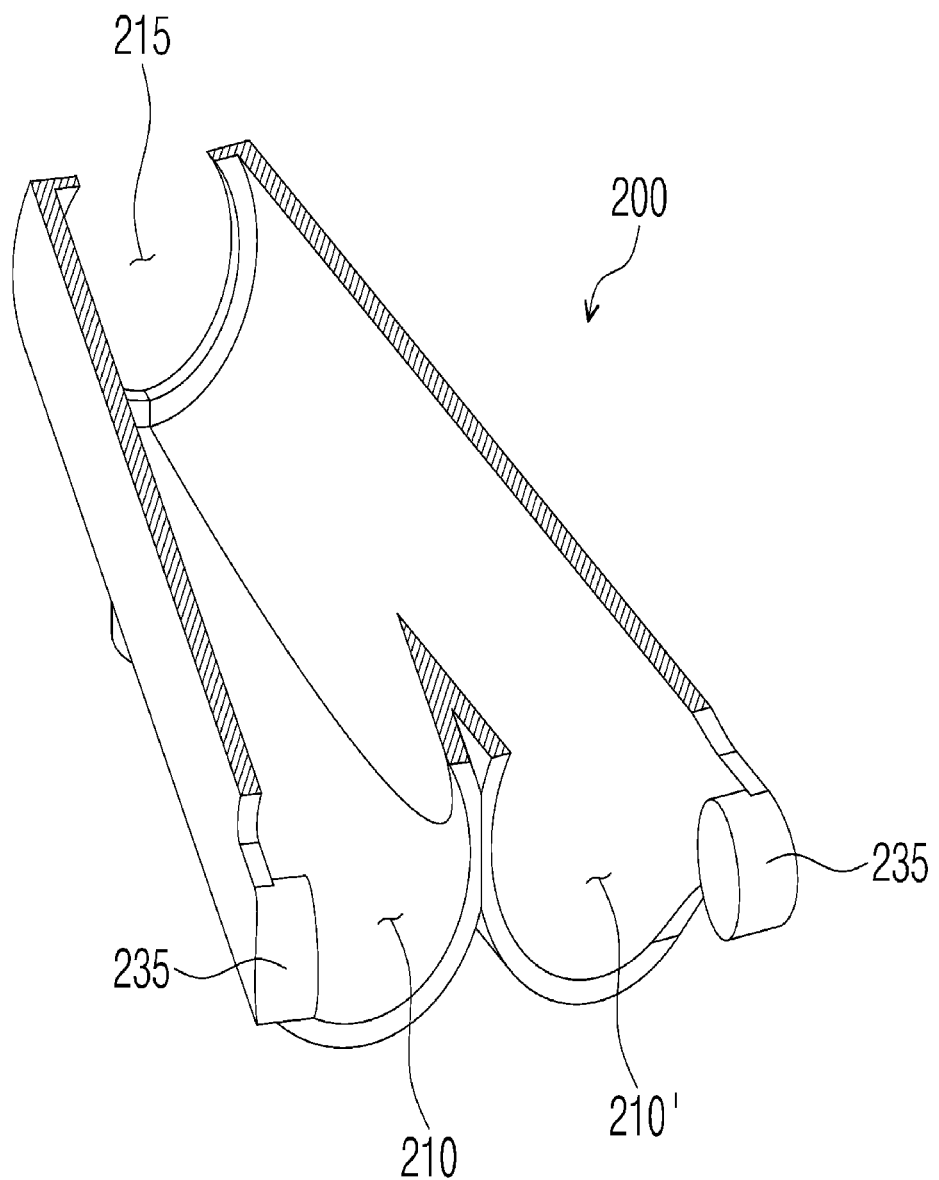
FIG. 4 is a partially-sectioned perspective view schematically showing an aligning holder unit in the percutaneous screw fixing rod inserting device for minimal invasive surgery according to an embodiment of the present disclosure.
Figure 5:
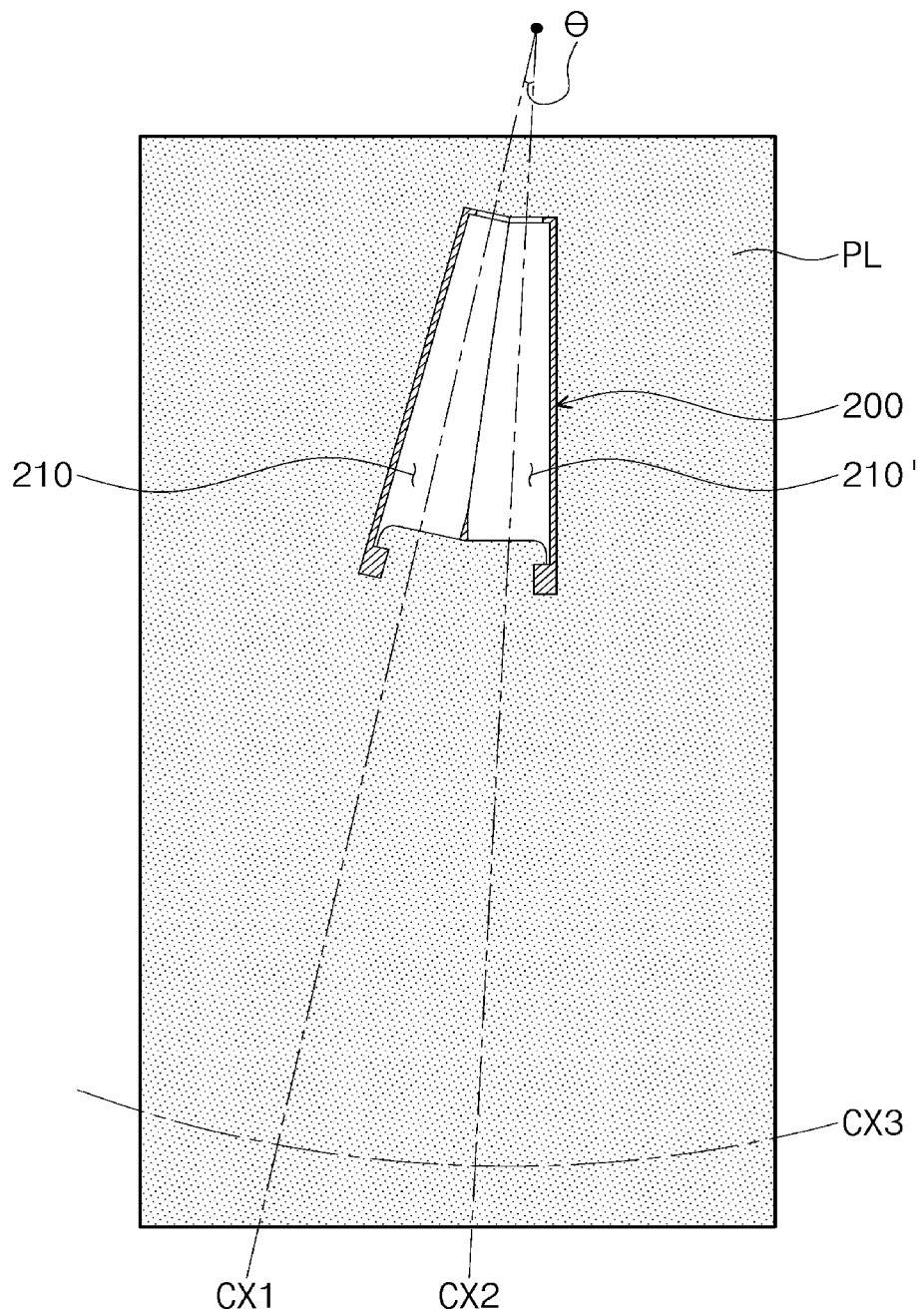
FIG. 5 is a side sectional view schematically showing the aligning holder unit in the percutaneous screw fixing rod inserting device for minimal invasive surgery according to an embodiment of the present disclosure.
Figure 6:
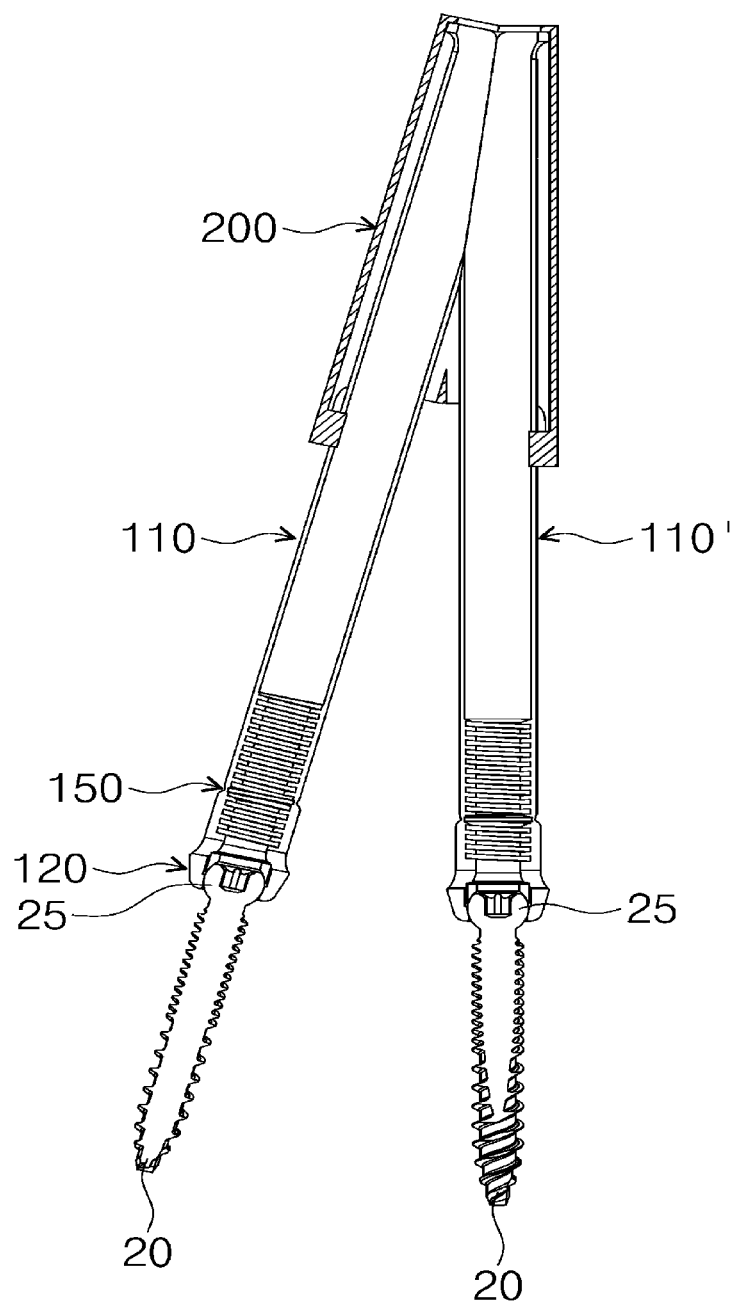
FIG. 6 is a side sectional view schematically showing the leg unit and the aligning holder unit in the percutaneous screw fixing rod inserting device for minimal invasive surgery according to an embodiment of the present disclosure.

FIG. 4 is a partially-sectioned perspective view schematically showing an aligning holder unit in the percutaneous screw fixing rod inserting device for minimal invasive surgery according to an embodiment of the present disclosure, FIG. 5 is a side sectional view schematically showing the aligning holder unit in the percutaneous screw fixing rod inserting device for minimal invasive surgery according to an embodiment of the present disclosure, and FIG. 6 is a side sectional view schematically showing the leg unit and the aligning holder unit in the percutaneous screw fixing rod inserting device for minimal invasive surgery according to an embodiment of the present disclosure.

Referring to FIGS. 4 to 6, the aligning holder unit 200 aligns the plurality of support legs 110, 110' so that longitudinal central axes CX1, CX2 of the support legs 110, 110' of the leg unit 100 are placed on one virtual plane PL, but holds the support leg 110, 110' so that an angle (θ) between the longitudinal central axes CX1, CX2 of the support legs 110, 110' may be maintained.

In addition, as mentioned above in relation to the rod insert hole 125, the rod insert hole 125 is formed in the joint link 120 so that a central axis CX3 of rod 30 may be placed on the same virtual plane PL where the longitudinal central axes CX1, CX2 of the support legs 110, 110' are placed. Thus, the rod 30 may be inserted in a state where the alignment is maintained.

Therefore, the difficulty in inserting the rod 30 caused by the misalignment of the pedicle screw 20 is eliminated.

In addition, the partial upper portions 115 of the support legs 110, 110' are inclined so that the angle (θ) may be set between the longitudinal central axes CX1, CX2 as the partial upper portions 115 of the neighboring support legs 110, 110' come into contact with each other.

Moreover, the aligning holder unit 200 has leg holding holes 210, 210' so that the partial upper portions of the support legs 110, 110' may be inserted into and held in the aligning holder unit 200.

Here, a plurality leg holding holes 210, 210' are provided such that the plurality of support legs 110, 110' may be respectively inserted therein, and partial upper portions of the plurality of support legs 110, 110' are respectively inserted into the leg holding holes 210, 210' of the aligning holder unit 200' so that the inclined partial upper portions 115 of the neighboring support legs 110, 110' are held in contact with each other.

In addition, at the lower side of the aligning holder unit 200, the leg holding holes 210, 210' are formed distinguishably so that partial upper portions of the plurality of support legs 110, 110' may be individually inserted therein.

At the inner side of the aligning holder unit 200, the leg holding holes 210, 210' are formed to correspond to the outer surface of the plurality of support legs 110, 110' whose partial upper portions are in contact with each other. Therefore, the support legs 110, 110' inserted into the leg holding holes 210, 210' are held by the aligning holder unit 200.

A center hole 215 is formed at an upper end of the aligning holder unit 200 to communicate with the leg holding hole 210, 210'. Also, an empty space 130 is provided inside the support leg 110, 110'.

Therefore, the pedicle screw 20 inserted into the center hole 215 may be moved to the joint link 120 provided at the lower end of the support leg 110, 110' and fixed to the spine.

An aligning guide protrusion 235 is provided at the lower end of the aligning holder unit 200 such that at least a portion of the aligning guide protrusion 235 is inserted into the aligning guide hole 135 of the support leg 110, 110' to guide the support leg 110, 110' to be inserted into the leg holding hole 210, 210' of the aligning holder unit 200 in a longitudinal direction.

At least a portion of the aligning guide protrusion 235 is inserted into the aligning guide hole 135 to prevent the support leg 110, 110' from rotating around the longitudinal central axis CX1, CX2.

Next, the rod inserting unit 300 will be described with reference to FIG. 7.

Figure 7:
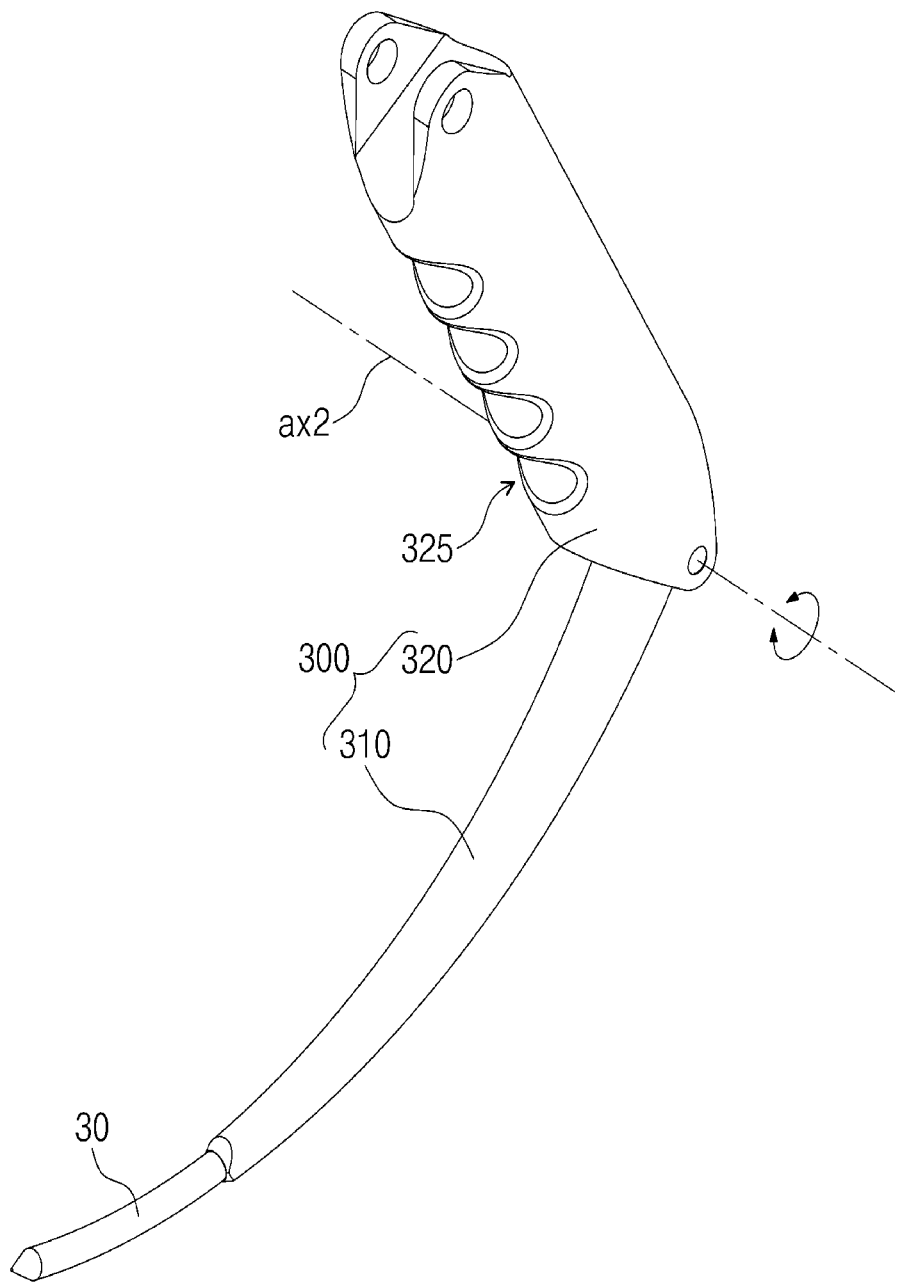
FIG. 7 is a perspective view schematically showing a rod inserting unit in the percutaneous screw fixing rod inserting device for minimal invasive surgery according to an embodiment of the present disclosure.

FIG. 7 is a perspective view schematically showing a rod inserting unit in the percutaneous screw fixing rod inserting device for minimal invasive surgery according to an embodiment of the present disclosure.

The rod inserting unit 300 is detachably coupled to the aligning holder unit 200. In addition, as shown in FIG. 8, the rod inserting unit 300 may rotate by a predetermined angle around a rotation axis ax1 of a portion 230 that is coupled to the aligning holder unit 200, and may insert the rod 30 into the rod insert hole 125 provided to the joint link 120 of the support leg 110, 110' to secure a gap between neighboring spines.

The rod inserting unit 300 includes a rod holder 310 and a swing body 320.

The rod holder 310 holds the rod 30 at one side end thereof so that the rod 30 may be selectively mounted thereto or detached therefrom.

One side end of the swing body 320 is hinged to the other side end of the rod holder 310 so that the rod holder 310 may rotate by a certain angle. Reference sign ax2 in FIG. 7 denotes a rotation axis according to this hinged coupling. In addition, the swing body 320 supports the hinged rod holder 310.

In addition, the other side end of the swing body 320 is coupled to a portion of the aligning holder unit 200, so that the swing body 320 may rotate by a certain angle around the rotation axis ax1 of the portion 230 that is coupled to the aligning holder unit 200.

Further, it is preferable that the coupling between the other side end of the swing body 320 and the aligning holder unit 200 is a selectively detachable coupling. If required, the user may manually detach the rod inserting unit 300 from the aligning holder unit 200, grip the swing body 320 of the rod inserting unit 300, and insert the rod 30 into the rod insert hole 125.

For the user to easily grip the swing body 320, the swing body 320 has a gripping groove 325 that may be gripped by a hand more easily.

As described above, according to the screw fixing rod inserting device 10 for minimal invasive surgery according to the present disclosure, the rod 30 may be inserted into the rod insert hole 125 in a state where the plurality of support legs 110, 110' are maintained in an aligned state.

Therefore, the difficulty in inserting the rod 30 caused by the misalignment of the pedicle screws 20 is eliminated, thereby increasing the convenience or efficiency of the medical procedure.

In addition, the present disclosure may be applied as shown in FIGS. 9 to 13.

Figure 9:
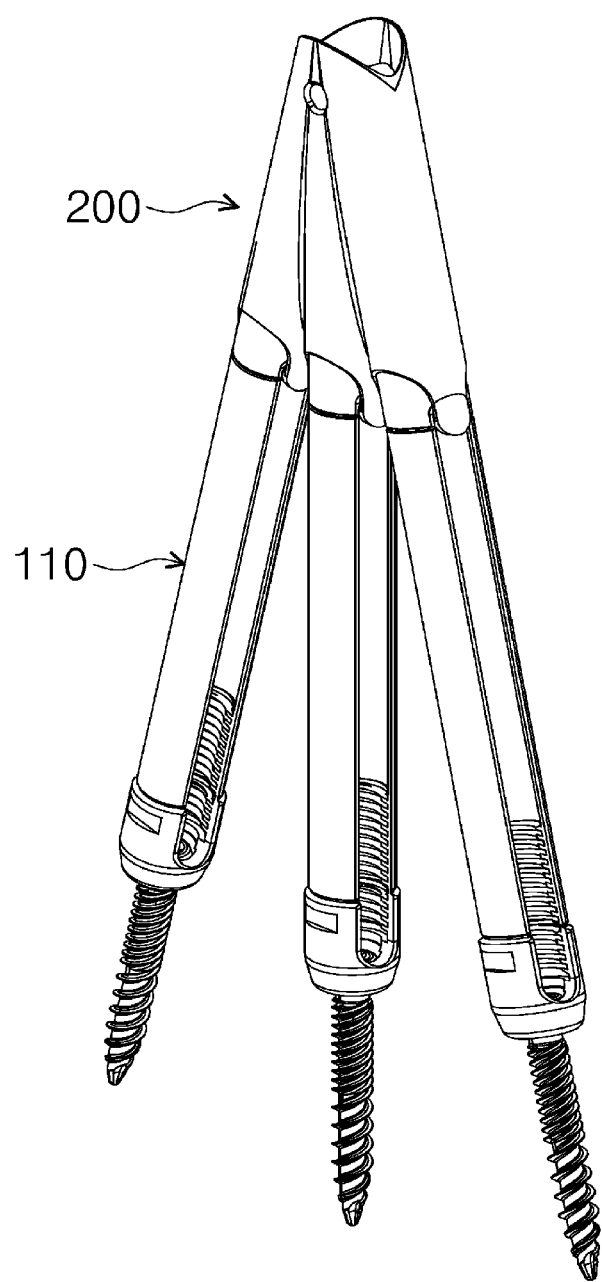
FIG. 9 is a perspective view schematically showing a portion of the percutaneous screw fixing rod inserting device for minimal invasive surgery according to an embodiment of the present disclosure in application.
Figure 10:
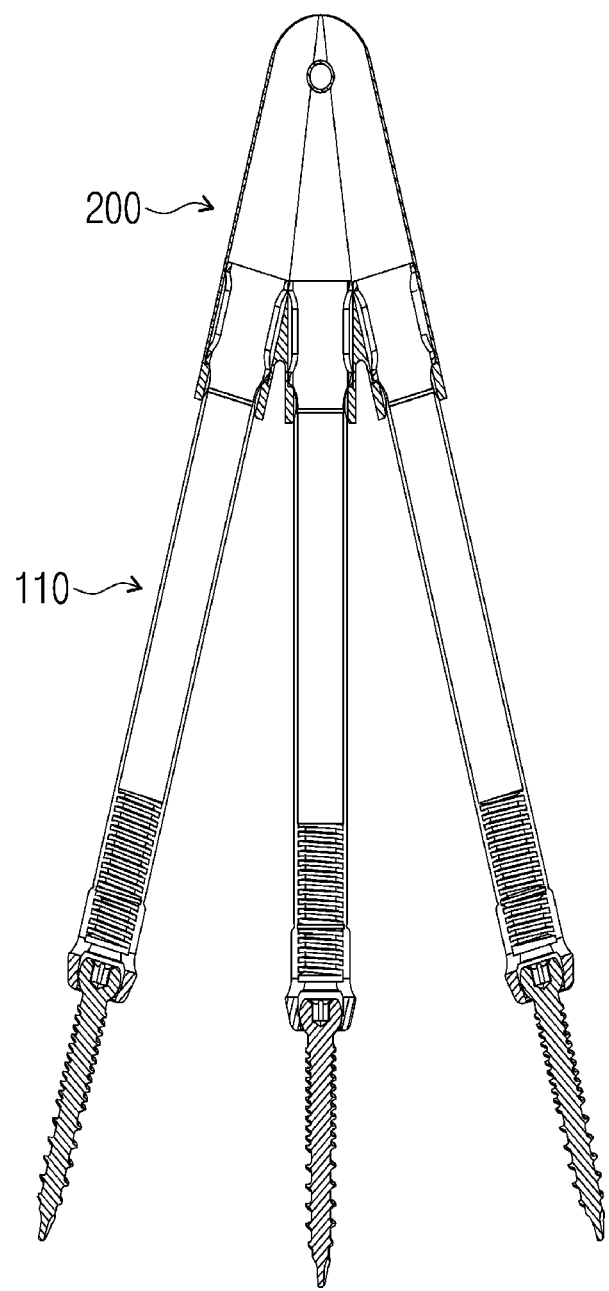
FIG. 10 is a sectional view schematically showing a portion of the percutaneous screw fixing rod inserting device for minimal invasive surgery according to an embodiment of the present disclosure in application.
Figure 11:
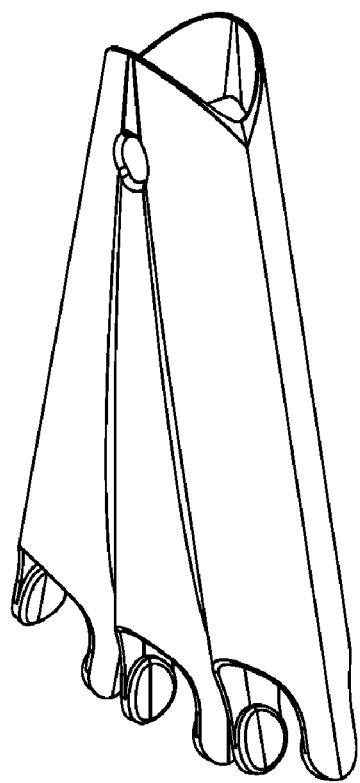
FIGS. 11 to 13 are diagrams schematically showing application forms of the aligning holder unit in the percutaneous screw fixing rod inserting device for minimal invasive surgery according to an embodiment of the present disclosure.
Figure 12:
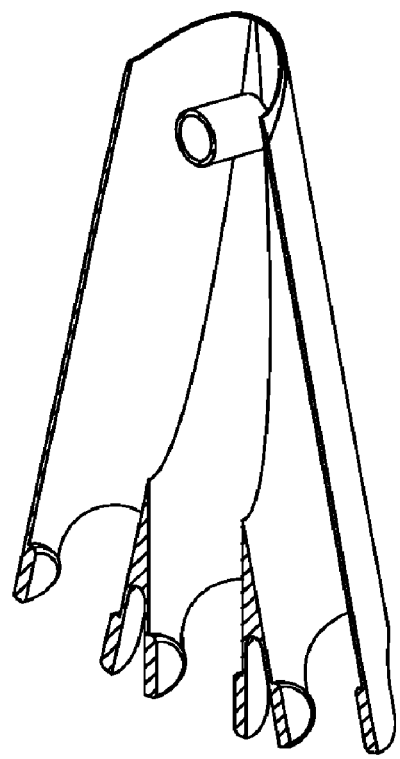
Figure 13:
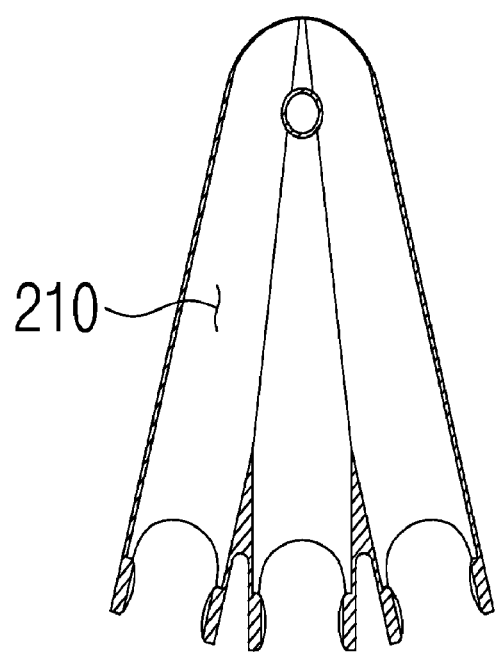

FIG. 9 is a perspective view schematically showing a portion of the percutaneous screw fixing rod inserting device for minimal invasive surgery according to an embodiment of the present disclosure in application, FIG. 10 is a sectional view schematically showing a portion of the percutaneous screw fixing rod inserting device for minimal invasive surgery according to an embodiment of the present disclosure in application, and FIGS. 11 to 13 are diagrams schematically showing application forms of the aligning holder unit in the percutaneous screw fixing rod inserting device for minimal invasive surgery according to an embodiment of the present disclosure.

As shown in FIGS. 9 to 13, three support legs 110 may be provided, and the aligning holder unit 200 may be configured to hold three support legs 110. The aligning holder unit 200 has the leg holding holes 210 in a distinguishable form so that three support legs 110 may be stably held.

In addition, modified forms as shown in FIGS. 14 to 18 may also be possible.

Figure 14:
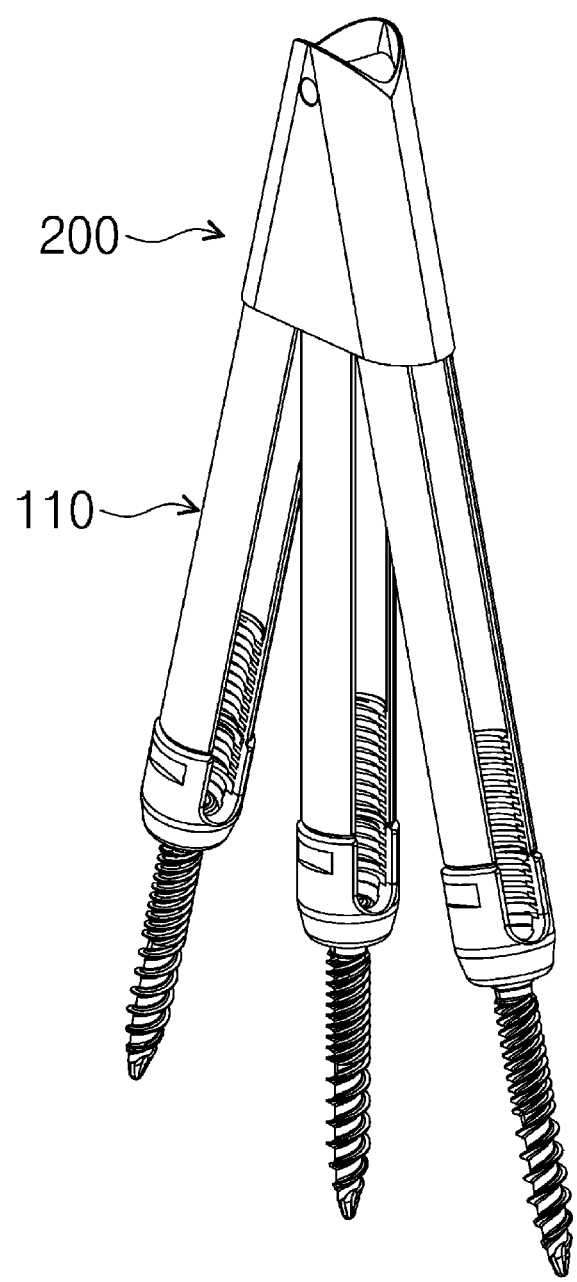
FIG. 14 is a perspective view schematically showing a modified portion of the percutaneous screw fixing rod inserting device for minimal invasive surgery according to an embodiment of the present disclosure.
Figure 15:
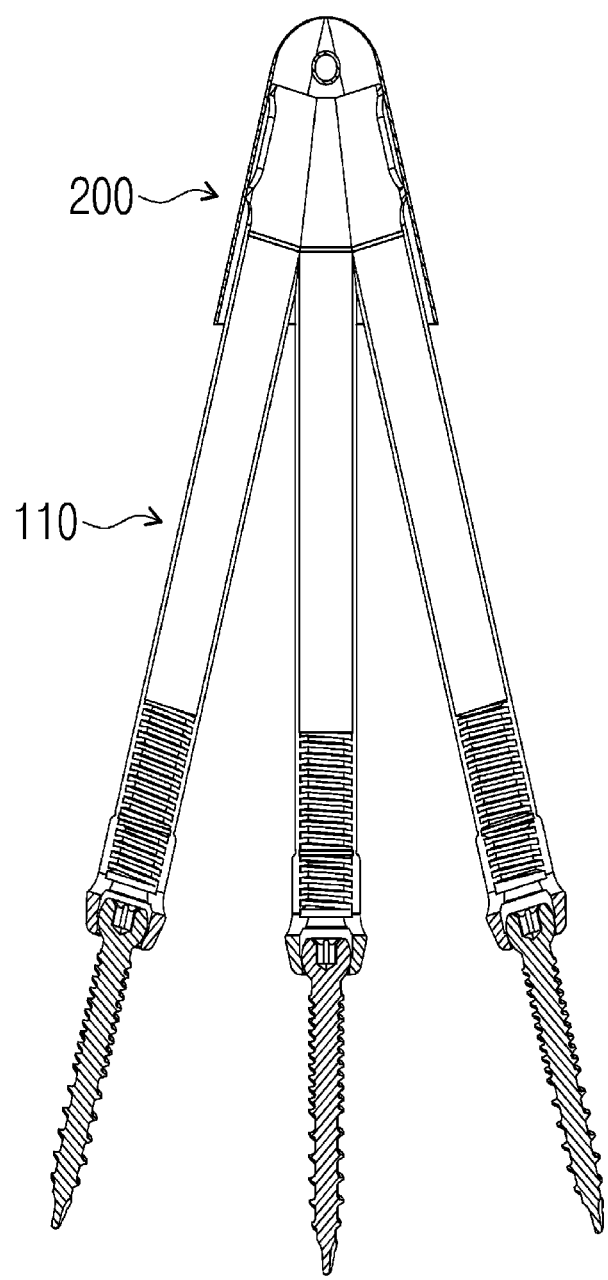
FIG. 15 is a sectional view schematically showing a modified portion of the percutaneous screw fixing rod inserting device for minimal invasive surgery according to an embodiment of the present disclosure.
Figure 16:
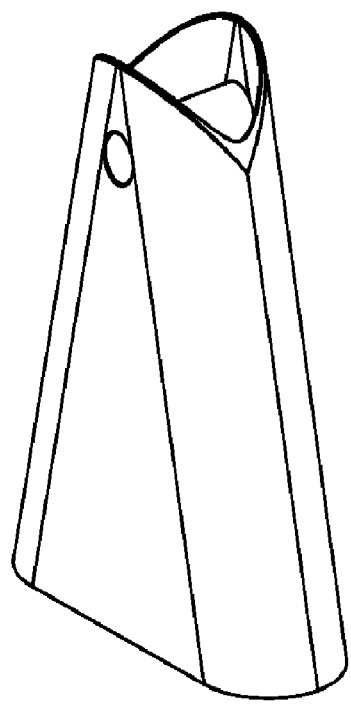
FIGS. 16 to 18 are diagrams schematically showing modified forms of the aligning holder unit in the percutaneous screw fixing rod inserting device for minimal invasive surgery according to an embodiment of the present disclosure.
Figure 17:
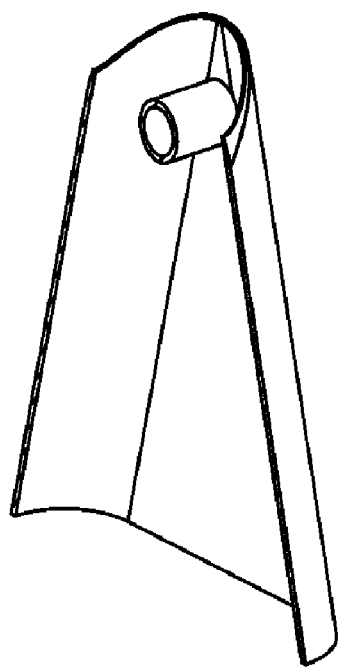
Figure 18:
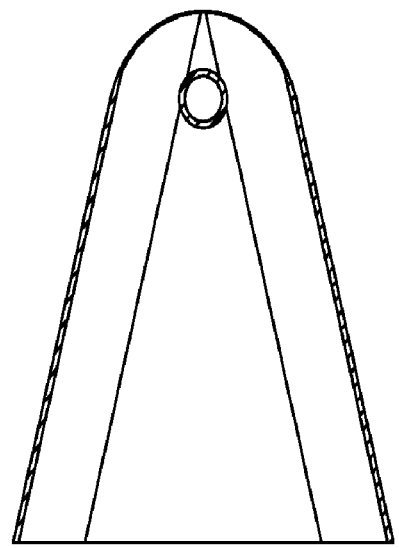

FIG. 14 is a perspective view schematically showing a modified portion of the percutaneous screw fixing rod inserting device for minimal invasive surgery according to an embodiment of the present disclosure, FIG. 15 is a sectional view schematically showing a modified portion of the percutaneous screw fixing rod inserting device for minimal invasive surgery according to an embodiment of the present disclosure, and FIGS. 16 to 18 are diagrams schematically showing modified forms of the aligning holder unit in the percutaneous screw fixing rod inserting device for minimal invasive surgery according to an embodiment of the present disclosure.

As shown in FIGS. 14 to 18, three support legs 110 may be provided, and the aligning holder unit 200 may be configured to hold three support legs 110. The aligning holder unit 200 has the leg holding hole 210 that holds three support legs 110 to cover the support legs 110 together.

The present disclosure may be applied or modified variously as above.

As described above, the present disclosure has been described in detail based on the embodiments with reference to the accompanying drawings, but the embodiments are just preferred examples of the present disclosure. Therefore, the present disclosure should not be construed as being limited to the above embodiments, and the scope of the present disclosure should be understood as being defined by the appended claims and their equivalents.

| [Reference Numerals] | |
|---|---|
| 10: percutaneous screw fixing rod inserting device for minimal invasive surgery | |
| 20: pedicle screw | 30: rod |
| 25: screw head | |
| 100: leg unit | |
| 110, 110': support leg | 120: joint link |
| 115: partial upper portion | |
| 125: rod insert hole | 135: aligning guide hole |
| 130: empty space | |
| 150: segmentation groove | |
| 200: aligning holder unit | |
| 210, 210': leg holding hole | 215: center hole |
| 230: portion of swing body | |
| 235: aligning guide protrusion | |
| 300: rod inserting unit | |
| 310: rod holder | 320: swing body |
| 325: gripping groove | |

The invention claimed is:

1. A percutaneous screw fixing rod inserting device for minimal invasive surgery, the device comprising:
   a leg unit including a plurality of support legs, each of the plurality of support legs having a joint link disposed at a lower end thereof, wherein the joint link includes a rod insert hole and is configured to mediate coupling between a rod and a screw head of a pedicle screw configured to fix to a spine;
   an aligning holder unit holding the plurality of support legs and configured to align the plurality of support legs, wherein longitudinal central axes of the plurality of support legs are on one virtual plane and an angle between the longitudinal central axes of the plurality of support legs is maintained; and
   a rod inserting unit coupled to the aligning holder unit and configured to rotate by a predetermined angle around a portion coupled to the aligning holder unit and to insert the rod into the rod insert hole of the joint link of the each of the plurality of support legs, wherein the each of the plurality of support legs has a partial upper portion which is inclined and the partial upper portions of adjacent support legs come into contact with each other to set the angle between the longitudinal central axes thereof, wherein the aligning holder unit has a plurality of leg holding holes and the partial upper portion of the each of the plurality of support legs are respectively inserted into and held in corresponding each of the plurality of leg holding holes, wherein the each of the plurality of support legs has an aligning guide hole formed by cutting at least a portion of an outer circumference of the support leg in a longitudinal direction, and wherein the each of the plurality of leg holding holes has an aligning guide protrusion formed adjacent thereto, and at least a portion of the aligning guide protrusion is configured to be inserted into a corresponding aligning guide hole of the support leg and to guide the support leg to be inserted into the leg holding hole of the aligning holder unit in the longitudinal direction.

2. A percutaneous screw fixing rod inserting device for minimal invasive surgery, the device comprising:

a leg unit including a plurality of support legs, each of the plurality of support legs having a joint link disposed at a lower end thereof, wherein each joint link includes a rod insert hole and is configured to mediate coupling between a rod and a screw head of a pedicle screw among a plurality of pedicle screws configured to fix to a spine;

an aligning holder unit holding the plurality of support legs and configured to align the plurality of support legs, wherein longitudinal central axes of the plurality of support legs are on one virtual plane and an angle between the longitudinal central axes of the plurality of support legs is maintained; and a rod inserting unit coupled to the aligning holder unit and configured to rotate by a predetermined angle around a portion coupled to the aligning holder unit and to insert the rod into the rod insert hole of the joint link of the each of the plurality of support legs, wherein the each of the plurality of support legs has a partial upper portion which is inclined and the partial upper portions of adjacent support legs come into contact with each other to set the angle between the longitudinal central axes thereof, wherein the aligning holder unit has a plurality of leg holding holes and the partial upper portion of the each of the plurality of support legs are respectively inserted into and held in corresponding each of the plurality of leg holding holes, wherein the plurality of leg holding holes are formed at a lower side of the aligning holder unit and the partial upper portions of the plurality of support legs are respectively inserted therein, and wherein at an inner side of the aligning holder unit, the plurality of leg holding holes are shaped corresponding to a shape of outer surfaces of the plurality of support legs whose partial upper portions are in contact with each other.

3. The device of claim 2, wherein the aligning holder unit has a center hole formed at an upper end thereof to communicate with the plurality of leg holding holes, wherein the each of the plurality of support legs has an empty space formed therein, and wherein each of the plurality of pedicles screws is configured to be inserted into the center hole, move to a corresponding joint link disposed at the lower end of a corresponding support leg, and to be fixed to the spine.

4. The device of claim 3, wherein the each of the plurality of support legs has an aligning guide hole formed by cutting at least a portion of an outer circumference of the corresponding support leg in a longitudinal direction, and wherein the each of the plurality of leg holding holes has an aligning guide protrusion formed adjacent thereto, and at least a portion of each aligning guide protrusion is configured to be inserted into a corresponding aligning guide hole of the corresponding support leg and to guide the corresponding support leg to be inserted into a corresponding leg holding hole of the aligning holder unit in the longitudinal direction.

5. The device of claim 4, wherein the portion of each of the aligning guide protrusions is configured to be inserted into the corresponding aligning guide hole and prevent the plurality of support legs from rotating around a longitudinal central axis thereof.

6. The device of claim 5, wherein a segmentation groove is formed at an upper side of the each joint link and the each joint link is configured to separate from the corresponding support leg.

7. The device of claim 6, wherein the rod inserting unit comprises:

a rod holder configured to hold the rod at one side end thereof, wherein the rod is selectively mounted thereto or detached therefrom; and a swing body supporting the rod holder and having one side end thereof hinge coupled to an other side end of the rod holder, wherein the rod holder is configured to rotate by a certain angle.

8. The device of claim 7, wherein an other side end of the swing body is coupled to a portion of the aligning holder unit, and the swing body is configured to rotate by the certain angle around the coupled portion.

9. The device of claim 8, wherein the other side end of the swing body and the portion of the aligning holder unit is selectively and detachably coupled.

* * * * *